United States Patent [19]

Voronkov et al.

[11] Patent Number: 4,468,378
[45] Date of Patent: Aug. 28, 1984

[54] OXYSULFONIC DERIVATIVE OF COPOLYMER OF ACROLEIN AND ACRYLIC ACID AND DIRECT ACTION ANTICOAGULANT ON ITS BASIS

[76] Inventors: Mikhail G. Voronkov, ulitsa Lermontova, 315, kv. 32; Ada T. Platonova, ulitsa Lermontova, 313, kv. 31; Vladislava Z. Annenkova, ulitsa Marata, 29, kv. 16; Valentina M. Annenkova, ulitsa Lermontova, 289, kv. 43; Valentina B. Kazimirovskaya, ulitsa Lermontova, 289, kv. 56; Galina S. Ugrjumova, ulitsa Lermontova, 303, kv. 48, all of Irkutsk, U.S.S.R.

[21] Appl. No.: 268,202

[22] Filed: May 29, 1981

Related U.S. Application Data

[62] Division of Ser. No. 169,242, Jul. 16, 1980, abandoned.

[51] Int. Cl.$^3$ .............................................. A61K 31/78
[52] U.S. Cl. ............................. 424/81; 128/DIG. 22; 526/287
[58] Field of Search ................... 128/DIG. 22, 334 R; 424/78, 79, 81; 525/344

[56] References Cited

U.S. PATENT DOCUMENTS 3,129,195  4/1964  June ................................... 526/287

FOREIGN PATENT DOCUMENTS 0010621  9/1979  European Pat. Off. .

Primary Examiner—Christopher A. Henderson
Attorney, Agent, or Firm—Ladas & Parry

[57] ABSTRACT

According to the invention, the oxysulfonic derivative of the copolymer of acrolein and acrylic acid is of the following formula:

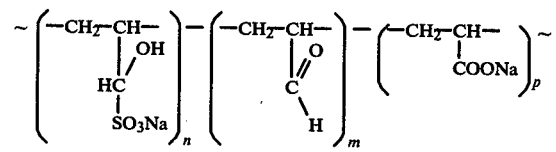

where n=190 to 600, m=190 to 500, and p=830 to 850. This biologically active compound can be used as a direct and prolonged action blood antiacoagulant to be administered in the form of 1- or 2-percent solutions. The preparation according to the invention features a long shelf and has a longer action than the well-known heparin.

2 Claims, No Drawings

OXYSULFONIC DERIVATIVE OF COPOLYMER OF ACROLEIN AND ACRYLIC ACID AND DIRECT ACTION ANTICOAGULANT ON ITS BASIS

This is a continuation of application Ser. No. 169,242 filed July 16, 1980, now abandoned.

FIELD OF THE INVENTION

The present invention relates to polymers intended for medical applications and, more particularly, to an oxysulfonic derivative of the copolymer of acrolein and acrylic acid and a direct-action anticoagulant of blood produced on its basis.

BACKGROUND OF THE INVENTION

Anticoagulants of blood are divided into those of direct and indirect action. While there is a great variety of indirect-action anticoagulants, synthetic anticoagulants of direct action are practically non-existent.

Direct-action anticoagulants prevent thrombogenesis, for which reason they are of great help in treating cases of myocardial infarction, pulmonary embolism and other diseases leading to acute thrombosis.

The significance of producing new direct-action anticoagulants of blood is apparent in view of the current spread of cardiovacular disorders.

Today, the commonest direct-action anticoagulant of blood is heparin which is an ester of sulfurinc acid and mucopolysaccharide. This natural product is prepared from lung tissues of bovine animals. Heparin is quite expensive, although its effect wears off in four or five hours. The known synthetic direct-action anticoagulants include sulfonated hydrolyzate of pectin according to Swiss Pat. No. 342,556 of Jan. 15, 1970; sulfonated starch (cf. Sigiura Mamoru, Sigiura Shoji, Yamamoto Hajime, Polia Pharmacol. Jap., 69, No 5, pp. 689–693, 1973); sulfonated chitosan (cf. I. G. Kochnev, V. M. Molodkin et al., Zhurnal Polevoy Khirurghii/Journal of Field Surgery, 46, Series 6, pp. 1141–1142, 1973); derivatives of cis-1,4-polyisoprene containing aminosulfonate and carboxylic groups (cf. T. Beudeling, L. Van der Does, A. Bantjes, W. L. Sederel, J. Biomed. Mat. Res, 8, Nos 1, 2, p. 375, 1974); sulfonated polyvinylalcohol (cf. V. I. Shumakov, Experimentalnaya Khirurghiya (Experimental Surgery), No 1, 26, 1971); sodium polyethylene sulfonate (cf. M. Brüster, Klin. Wochenscher, 44, No 13, p. 766, 1966).

All the above compounds have proved to be unapplicable because of their toxicity and low anticoagulant effect.

There is further known a synthetic direct-action anticoagulant of blood prepared by sulfonating cellulose (cf. M. M. Kovaloyv, V. K. Tyoply, V. D. Yankovsky, N. A. Ivanova, A. F. Rekasheva, "Synantrine", Naukova Dumka Publishers, Kiev, 1974). The latter compound, too, is relatively toxic and features a short-lived effect.

SUMMARY OF THE INVENTION

It is an object of the present invention to broaden the nomenclature of compounds applicable as direct-action anticoagulants of blood.

The foregoing object is attained by providing a compound which is an oxysulfonic derivative of the copolymer of acrolein and acrylic acid of the general formula:

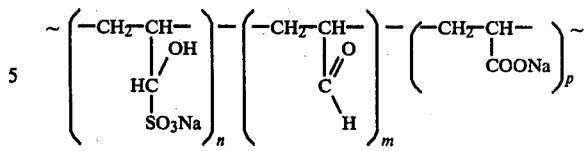

where $n = 190$ to $600$, $m = 190$ to $500$, and $p = 830$ to $850$.

The compound according to the invention is heretofore unknown and of great interest to medical workers in that it exhibits a specific biological activity.

DETAILED DESCRIPTION OF THE INVENTION

The oxysulfonic derivative of the copolymer of acrolein and acrylic acid of the above formula can be prepared by reacting the copolymer of acrolein and acrylic acid with an aqueous solution (5 to 10 percent by weight) of sulfurous anhydride during 10 to 20 hours at a temperature of 10 to 30° C., which is followed by a removal of excessive $SO_2$, neutralization of the solution with a caustic soda solution till $pH = 7$, and removal of the aqueous phase. The resulting compound of the foregoing formula is a white odorless powder which is readily soluble in water, has a long shelf life and starts to decompose at 150° C.

When introduced into the blood, aqueous solutions of the compound according to the invention exhibit a specific biological activity, slowing down or even completely stopping the coagulation process, which is indicative of a direct effect of this compound upon the blood.

The direct and prolonged action anticoagulant of this invention comprises a liquid carrier and an active principle which is the oxysulfonic derivative of the copolymer of acrolein and acrylic acid of the above formula. The compound's abbreviated name is "acrylsulfacrin".

According to the invention, acrylsulfacrin is produced by dissolving the oxysulfonic derivative of the above formula in water or 0.88-percent aqueous solution of sodium chloride. The active principle content in an aqueous solution is 1 to 2 percent by weight, which concentration is high enough to produce a desired effect. The preparation is stable during three or more years.

The specific activity of the oxysulfonic derivative of the copolymer of acrolein and acrylic acid of the foregoing formula was studied in vitro and in vivo on rabbits. In the course of the experiments, use was made of 0.88-percent aqueous solution of sodium chloride containing 1 percent by weight of the active principle.

The anticoagulation activity was quantitatively evaluated by means of a stabilization titer and standardized in units of heparin activity, the respective values being 1:10400 and 63.1 units.

The toxicity of acrylsulfacrin was studied on nondescript white mice. At an activity level of 63 units, $LD_{56}$ of the preparation was 350 mg/kg.

Investigation of hemocoagulation, involving incubation of blood plasma, showed the following effects of acrylsulfacrin upon the process of hemostasis:

(1) a reduced activity of the prothrombin complex factors;

(2) a dramatic prolongation of the thrombin period;

(3) an acceleration of the euglobulin lysis and partial formation of fibrin in the samples.

The anticoagulation action of acrylsulfacrin is neutralized by protamine sulfate. The proposed anticoagulant forms a soluble complex with fibrinogen.

Single intravenous injections of therapeutical doses of acrysulfacrin bring about the effects in the hemocoagulation system of test animals, which correspond to the effects of heparin. When administered in a therapeutical dose of 2.5 to 4.0 mg/kg, the action of acrysulfacrin lasts for 12 hours; a dose of 10 mg/kg accounts for a state of hypocoagulation which lasts for 24 or more hours.

Administration of acrylsulfacrin during 10 days in doses of 10 mg/kg (630 units) leads to a gradual intensification of the antithrombin and antithromboplastin activity of the blood plasma, which is maintained during 7 days after the administration is discontinued. Evaluation of the biochemical (residual nitrogen, sugar and protein) and hematologic (erythrocyte, thrombooyte and leukocyte counts, erythrocyte sedimentation rate, and hemoglobin estimation) blood characteristics did not reveal any serious malfunctions of the vital organs.

The survival rate of rabbits with induced thrombosis is increased by administering acrysulfacrin before the experiment.

Acrylsulfacrin has a number of important advantages over the known direct-action synthetic antociagulants. It is cheap and readily available and has a higher activity than conventional direct-action synthetic anticoagulants. It has a long shelf life of more than three years and features a prolonged effect. The initial products used in the preparation of acrysulfacrin, i.e. acrolein and acrylic acid, are common and readily available products of the chemical industry.

A better understanding of the present invention will be had from a consideration of the following examples illustrating the synthesis of the oxysulfonic derivative of the copolymer of acrolein and acrylic acid.

EXAMPLE 1

(A) 33.6 g (0.6 mole) of acrolein and 22.8 g (0.4 mole) of acrylic acid is placed in a four-neck flask provided with a stirrer, reflux condenser, thermometer and drop funnel. A solution containing 4.32 g of potassium persulfate in 150 ml of water is added. Intensified stirring follows, and a solution of 6.2 g of Mohr salt in 50 ml of water is added to the mixture. The polymerization takes 2 hours. The copolymer is collected on a filter, washed with water to remove unreacted monomers and initiators, and dried to constant weight. The copolymer yield is 80 to 90 percent.

(B) 1 g of the copolymer of acrolein and acrylic acid prepared as described in (A) is placed in 95 ml of 5-percent aqueous solution of sulfurous anhydride maintained at a temperature of 25° C. After 10 hours the unreacted sulfurous anhydride is removed, whereupon the reaction mass is warmed to 50° C. and is thus maintained, while being intensively stirred, during 3 to 5 hours. The solution is then neutralized to pH=7 by one-mole aqueous solution of caustic soda. The neutralized solution is dried, yielding the oxysulfonate derivative of the copolymer of acrolein and acrylic acid in the form of white, loose, water-soluble powder. The infrared spectrum of the copolymer has absorption bands of 950, 1080, 1380, 1560, 1640 and 1720 cm$^{-1}$. The initial decomposition point is 150° C.

The percentage composition is as follows: C, 40.18; H, 4,15; S, 4.42.

The end product is of the formula:

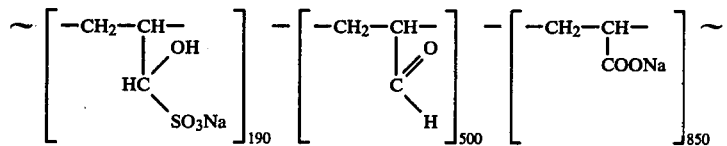

EXAMPLE 2

Under the conditions specified in Example 1(B), 10-percent aqueous solution of sulfurous anhydride is reacted for 20 hours at 25° C. with copolymer prepared as described in Example 1(A). The properties of the end product are similar to those of the product of Example 1.

The percentage composition of the product is as follows: C, 31.70; H, 3.39; S, 10.38.

The product is of the formula:

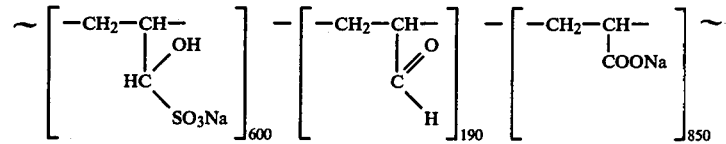

EXAMPLE 3

Under the conditions specified in Example 1(B), 10-percent aqueous solution of sulfurous anhydride is reacted during 10 hours with the copolymer of acrolein and acrylic acid prepared as described in Example 1(A). The properties of the oxysulfonic derivative thus produced are similar to those of the product of Example 1.

The percentage composition of the product is as follows: C, 34.72; H, 3.58; S, 7.96.

The end product is of the formula:

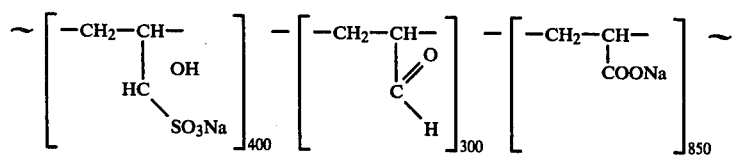

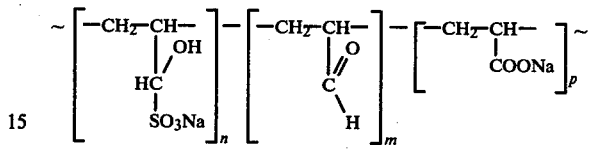

What is claimed is:

1. A direct and prolonged action low toxicity anticoagulant of blood, comprising an active principle which is an oxysulfonate derivative of the copolymer of acrolein and acrylic acid of the formula: and a liquid carrier for said active principle.

2. An anticoagulant of blood as claimed in claim 1, wherein the active principle content is 1 to 2 percent by weight.

* * * * *